United States Patent [19]
Hofmann et al.

[11] Patent Number: 5,704,908
[45] Date of Patent: *Jan. 6, 1998

[54] ELECTROPORATION AND IONTOPHORESIS CATHETER WITH POROUS BALLOON

[75] Inventors: Gunter A. Hofmann; Lois J. Crandell, both of San Diego, Calif.

[73] Assignee: Genetronics, Inc., San Diego, Calif.

[ * ] Notice: The term of this patent shall not extend beyond the expiration date of Pat. No. 5,304,120.

[21] Appl. No.: 729,007

[22] Filed: Oct. 10, 1996

[51] Int. Cl.$^6$ .................................................. A61N 1/30
[52] U.S. Cl. ............................................. 604/21; 604/96
[58] Field of Search ........................... 604/19–21, 96, 604/101

[56] References Cited

U.S. PATENT DOCUMENTS

| | | | |
|---|---|---|---|
| 5,286,254 | 2/1994 | Shapland et al. | 604/21 |
| 5,304,120 | 4/1994 | Crandell et al. | 604/21 |
| 5,505,700 | 4/1996 | Leone et al. | 604/96 |
| 5,507,724 | 4/1996 | Hofmann et al. | 604/21 |

FOREIGN PATENT DOCUMENTS

| | | |
|---|---|---|
| 1069826 | 1/1984 | U.S.S.R. |
| 1146057 | 3/1985 | U.S.S.R. |

*Primary Examiner*—Mark Bockelman
*Assistant Examiner*—Ellen Tao
*Attorney, Agent, or Firm*—Baker, Maxham, Jester & Meador

[57] ABSTRACT

An electroporation apparatus for introducing molecules into cells at a selected location within a cavity in the body of a patient includes an elongated catheter having a proximal end and a distal end and a guide wire extending from the proximal end to the distal end, an inflatable balloon carried by the distal end, the balloon having an inner inflatable bladder and an outer perforated bladder defining a chamber between the two bladders, a first electrode on an outer surface of the outer perforated bladder, a second electrode spaced from the first electrode, a remote electrode, a lumen for delivering a predetermined quantity of a fluid medium carrying preselected molecules into the chamber to be infused into the body cavity at the predetermined location; and a source of power for applying a voltage pulse between selected pairs of the electrodes for transport of the molecules by iontophoresis and/or repeatedly generating electric fields of a predetermined amplitude and duration inducing the walls of a plurality of cells at the predetermined location to be transiently permeable to enable the molecules to enter the cells.

25 Claims, 6 Drawing Sheets

5,704,908

ELECTROPORATION AND IONTOPHORESIS CATHETER WITH POROUS BALLOON

BACKGROUND OF THE INVENTION

The present invention relates to catheters for use in the treatment of ailments in humans and other mammals, and more particularly, to an improved electroporation catheter and method for delivering drugs and genes into the endothelial and other nearby cells of a patient.

In a prior U.S. Pat. No. 5,507,724 entitled "ELECTROPORATION AND IONTOPHORESIS APPARATUS AND METHOD FOR INSERTION OF DRUGS AND GENES INTO ENDOTHELIAL CELLS", there is disclosed a catheter device which is inserted into a selected blood vessel of a patient and advanced to a preselected location within the blood vessel where the endothelial cells on the inner wall of the vessel are to be treated. Once in place, the catheter device is expanded so that a plurality of axially extending, circumferentially spaced electrodes carried thereby are in contact with the inner wall of the blood vessel. A fluid medium is then infused into the blood vessel adjacent the electrodes via infusion ports communicating by supply lines from a conventional pump. A power pack connected to the electrodes is energized to apply a predetermined voltage pulse to the electrodes and generate electric fields of predetermined amplitude. This subjects the endothelial cells to electric fields of predetermined amplitude and duration in making the walls of the endothelial cells transiently permeable to permit therapeutic genes or drugs carried by the fluid medium to enter the endothelial cells without killing them.

Endothelial cells are in direct contact with the blood stream and cover almost one thousand square meters of the inner surface of the blood vessels of a human. The blood vessels extend throughout the body and closely adjacent to almost all tissue of the body. The invention of the above patent was developed primarily to treat damage to endothelial cells which has been linked to cardiovascular diseases such as arteriosclerosis and high blood pressure. Endothelial cell damage may result from surgical procedures such as heart transplantation and by balloon angioplasty and routing of the blood vessels with rotary and laser catheters. These procedures are frequently used to remove blockage in the coronary arteries, however, the resulting trauma and scarring to the lumen walls can lead to rapid return of fatty deposits and a recurrence of blockage.

Our studies have indicated that genetic modification of the endothelial cells might correct certain damage caused by surgical procedures and could reduce the rate of deposit of low density cholesterol before and after surgical procedures. Insertion of drugs directly into the cells also appears to be effective to alleviate problems associated with damage to these cells.

The blood vessels can also be used to transport genes and drugs to areas for treatment of tissue and cells in areas adjacent to the vessels. They can also be used to place electric field generating means such as electrodes adjacent the areas to be treated. Electroporation in combination alone and with other means can be used with improved catheters of the present invention for delivery of genes and drugs via the blood vessels into endothelial and into other adjacent cells in the body to provide improved and extended drug and gene therapy.

Catheters of this type and the methods of the present invention can also be used to treat the walls or linings of other passages or cavities in the human and animal body. In this treatment, it is necessary to present an adequate supply of molecules to administer to the cells in contact with the surface of the walls of passage or cavity being treated. Therefore, it is desirable that means be available for effectively placing and confining the therapeutic fluid containing the molecules to the treated area during treatment.

It is also desirable that improved catheters for drug and gene delivery to cells and for electric field generation be available.

SUMMARY OF THE INVENTION

Accordingly, it is an object of the present invention to provide an improved apparatus and method of electroporation mediated, in vivo, drug and gene delivery into the endothelial and other cells of a patient.

It is another object of the present invention to provide an improved catheter apparatus for electroporation mediated, in vivo, intra cellular drug and gene delivery into the cells of a patient.

According to a primary aspect of the present invention a catheter device is provided with an expandable distal portion carrying one or more electrodes for engaging and generating electric fields in vessel walls, infusion means including multiple infusion ports for infusion of fluid medium for carrying genes and drugs, and sealing means for sealing off and confining the therapeutic medium to the area to be treated. The catheter is inserted into a selected blood vessel of a patient and advanced to a preselected location within the blood vessel where the endothelial or other cells on the inner wall of the vessel or cells nearby the blood vessel are to be treated. Once in place, the catheter device is expanded so that the treatment area is first sealed off and then at least one electrode carried thereby is expanded into contact with the inner wall of the blood vessel. A fluid medium is infused into the blood vessel and placed into contact with the vessel wall within the area adjacent the electrodes via the catheter and a conventional pump. A power pack connected to the electrodes is energized to apply a predetermined voltage pulse to the electrodes. This subjects the endothelial or other cells to electric fields of predetermined amplitude and duration in order to make the walls of the endothelial cells transiently permeable to permit therapeutic genes or drugs carried by the fluid medium to enter the cells. Alternatively, the electric field cannot be of a selected strength to enable the cells to pass through the blood vessel wall tissue into adjacent tissue or cells.

In accordance with another aspect of the invention the fluid medium carrying the genes or drugs serves as one or more of the conductors and pores open to the inside wall of the vessel act as microelectrodes.

In accordance with another aspect of the invention, the expandable distal portion of the catheter is formed of inner and outer expandable bladder with the outer bladder perforated to infuse the medium to adjacent cells or cells in adjacent tissue for treatment by electroporation.

In accordance with another aspect of the invention, an additional remote electrode outside the catheter may be used to transport the cells through the tissue into areas adjacent to and/or away from the blood vessel.

BRIEF DESCRIPTION OF THE DRAWINGS

Throughout the drawing figures like reference numerals refer to like parts.

FIG. 9 is a view like FIG. 5 of a still further embodiment of the invention.

DESCRIPTION OF THE PREFERRED EMBODIMENTS

Figure 1:
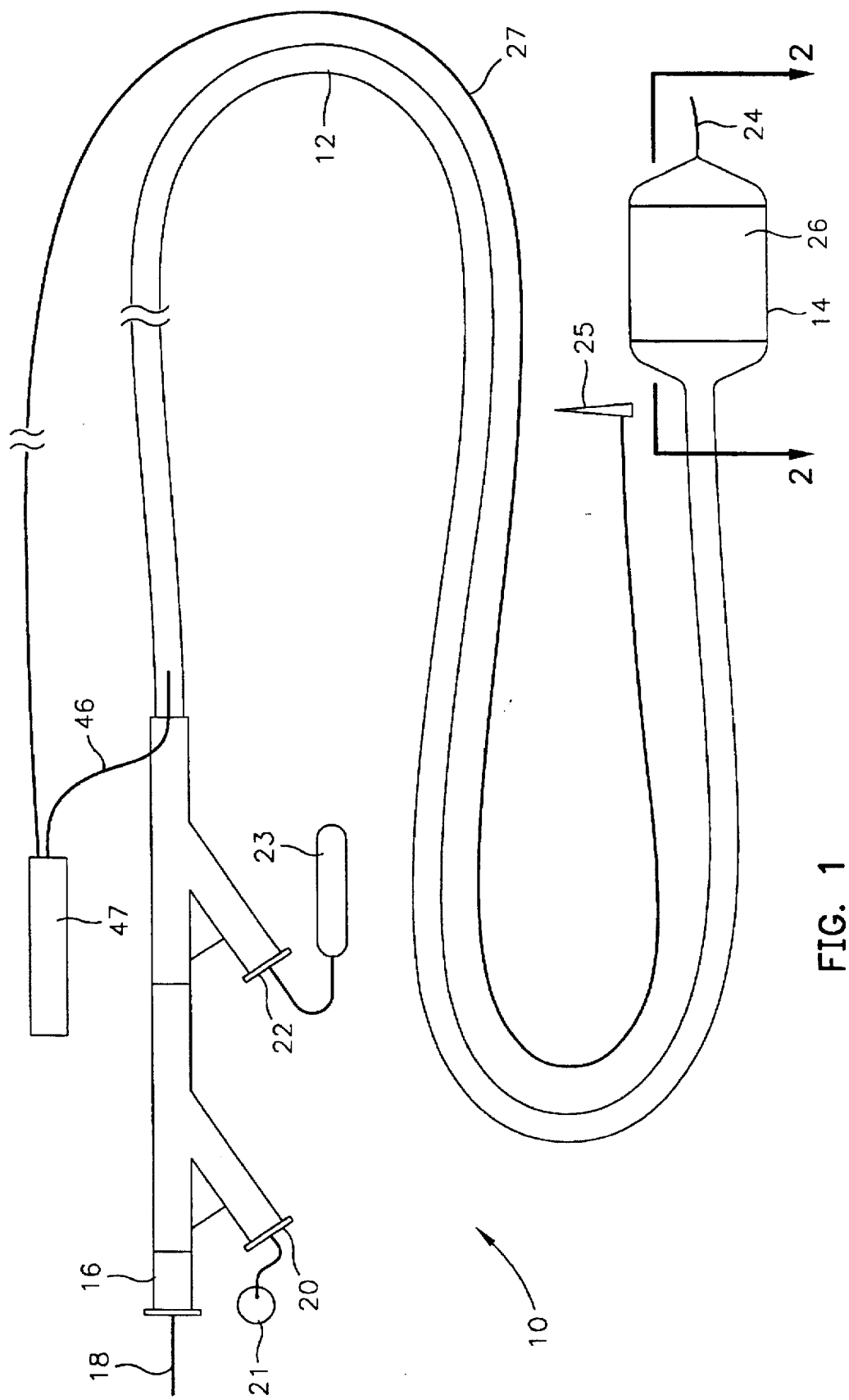
FIG. 1 is a plan view illustrating a catheter apparatus in accordance with the present invention.

Referring to FIGS. 1–4, a catheter designated generally by the numeral 10 in accordance a preferred embodiment of the invention is illustrated. The catheter 12 comprises an elongated flexible body member 12 having an expandable or inflatable distal end 14 and a proximal end 16 with a combined guide wire and electrical conductor 18. The catheter includes a drug or gene inlet or infusion inlet port 20 for connection to a source 21 of therapeutic fluid and an inflation port 22 at the proximal end thereof for connection to a source 23 of inflating medium, which may be a gas or liquid. The guide wire electrical conductor terminates at and forms an electrode at 24 at the distal end thereof. An opposing electrode which may preferably be in the form of a conductive coating 26 is carried on the outer surface of the inflatable portion 14 where it can contact or engage the blood vessel wall. The illustrated catheter is adapted to be inserted or implanted in a blood vessel of a patient which is to receive therapeutic treatment. However it is to be understood that the catheter construction and principles may be used for treatment of other organs or cavities of a human or animal body.

The system may also preferably include a remote electrode 25 connected by a conductor 27 to a power source 47. The electrode 25 may be designed to contact the surface of tissue or to penetrate into tissue such as a needle. This enables the use of iontophoresis to induce migration of molecules from where delivered by the catheter into tissue remote from that site. The electrode 25 can also be used in the electroporation mode. The catheter may be guided and inserted in a conventional manner by use of the guide wire 18.

Figure 2:
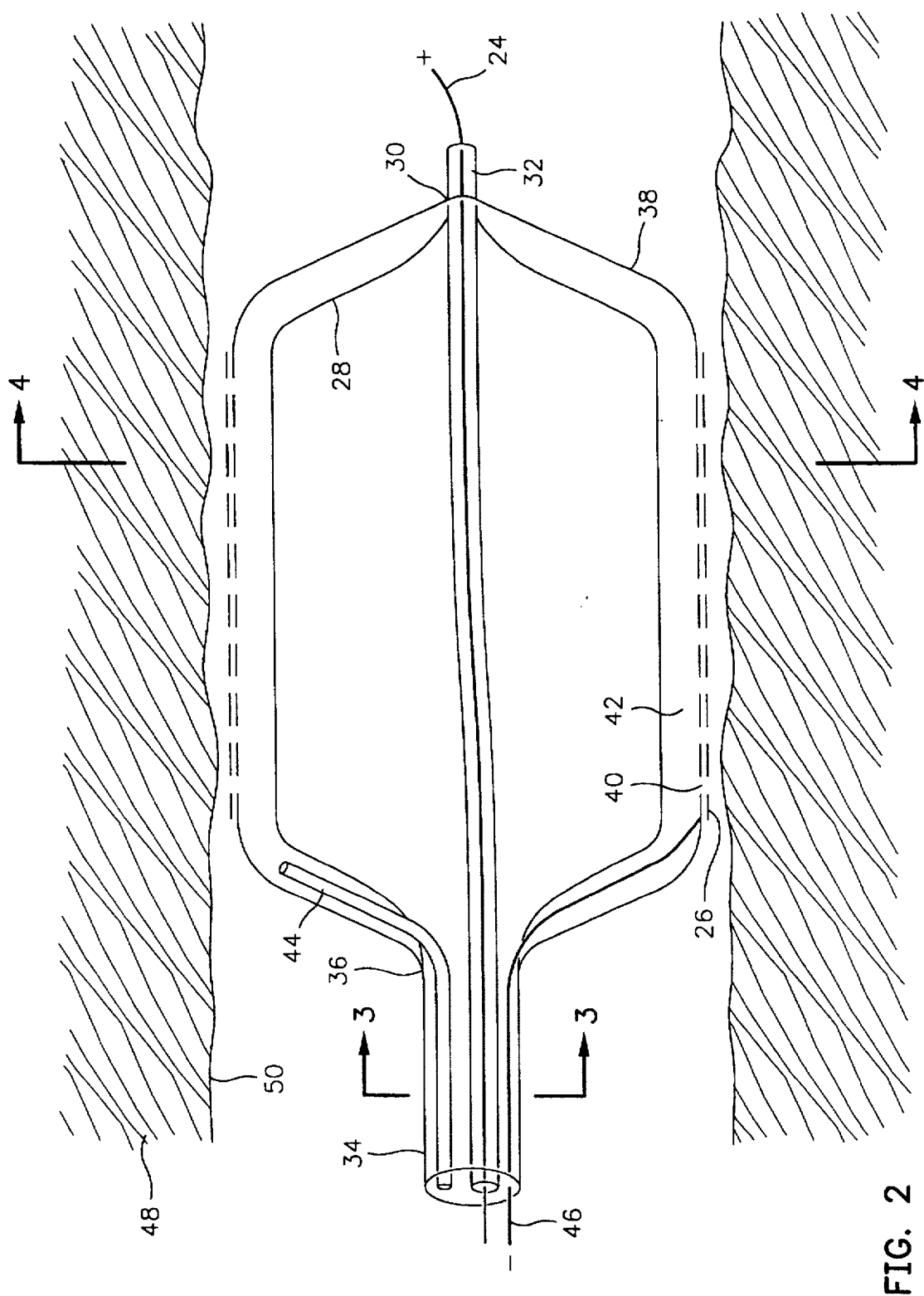
FIG. 2 is a detailed side elevation view of the embodiment of FIG. 1 shown inflated in the blood vessel.
Figure 3:
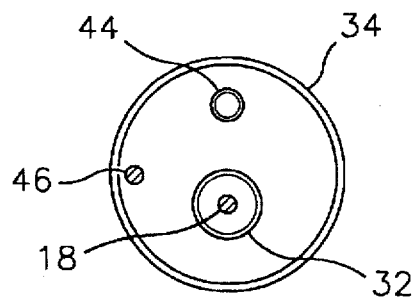
FIG. 3 a view taken generally on line 3—3 of FIG. 2.
Figure 4:
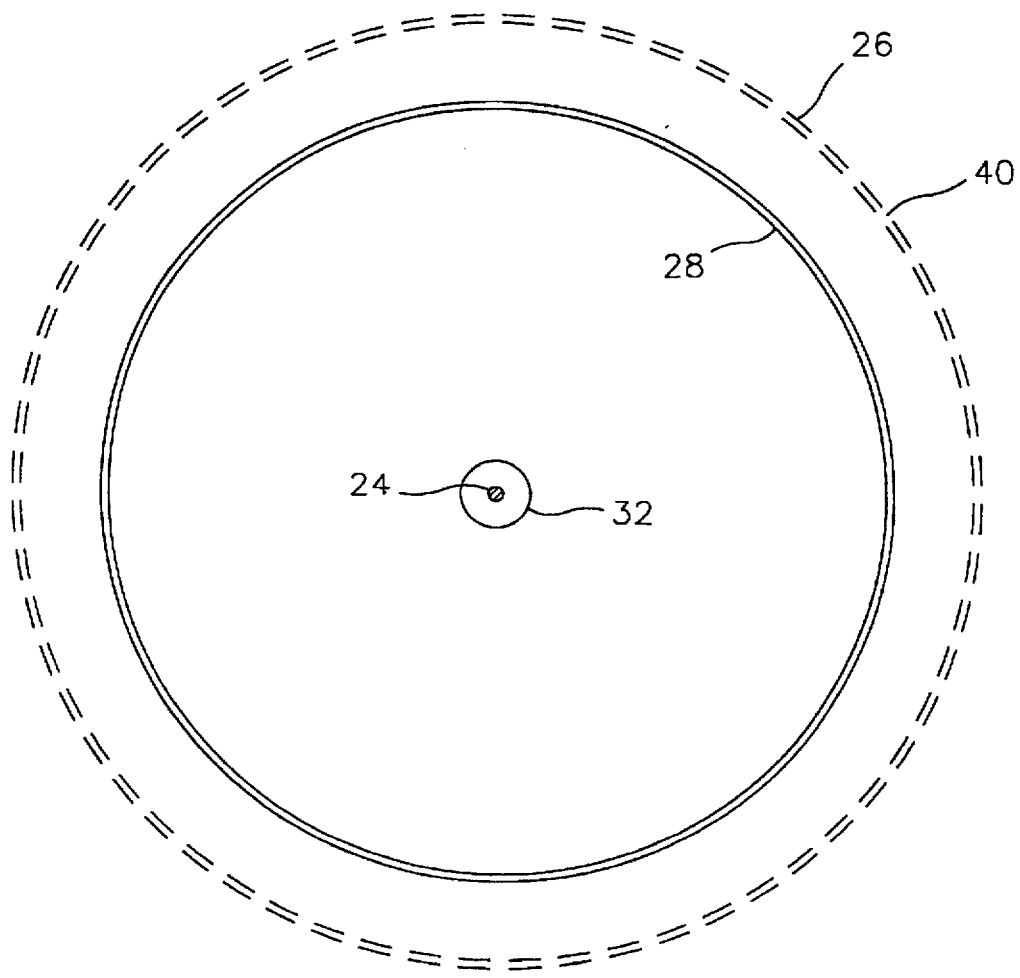
FIG. 4 is a view taken generally on line 3—3 of FIG. 2.
Figure 5:
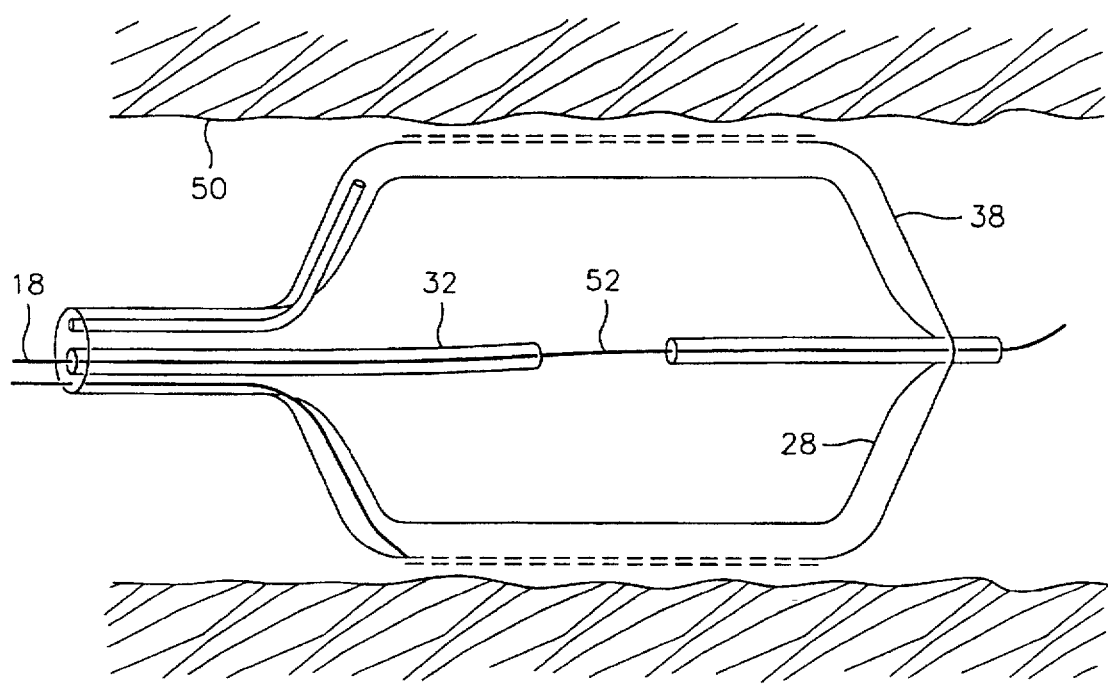
FIG. 5 is a side elevation view of an alternate embodiment of the invention shown in a blood vessel.

Referring to FIGS. 2–4 of the drawing, a preferred embodiment of the distal portion inflatable or expandable portion of the catheter is illustrated and shown expanded against blood vessel walls. In the illustrated embodiment, the inflatable distal portion 14 comprises an inner balloon or bladder 28 sealingly secured at an outermost end or portion 30 to a sheath 32 covering the guide wire and electrode 24. An inner end of the bladder or balloon 28 is sealingly connected to and communicates at 36 with a tubular sheath or covering 34 which extends to and communicates with the inflation port 22. An outer bladder 38 is disposed over the inner bladder 28 and sealingly secured at the same points 30 and 36 to the respective sheath or covers 32 and 34. This outer balloon 38 is perforated with a plurality of ports 40 for communicating fluid from an annular chamber 42 formed between the inner and outer bladders 28 and 38 to the blood vessel wall 50. A tube 44 communicates from the drug or gene inlet infusion port 20 at the proximal end of the catheter with the chamber 42 at the inflatable distal end of the catheter. The outer balloon 28 includes a conductive outer surface such as a coating 26 on at least the central circumferential portion thereof in conductive relationship with a conductor 46 which runs to and is connected and extends from the catheter at the proximal end thereof for connection to a source of electrical power, such as a pulse generator 47.

The electrode 25 (FIG. 1) may also be used by placing it into conductive contact with a tissue surface or by inserting it into tissue 48 as shown. This electrode can then be used in conjunction with either electrode 24 or 26 for either iontophoresis or for electroporation, or both.

The conductive surface or coating 26 may be of any suitable conductive coating material that is medically approved for contact with tissue and/or blood vessels of a patient. Such materials include silver, gold and conductive rubber, for example. The inflatable distal portion of the balloon is shown inside a vessel 48 with the outer bladder expanded into surface contact with the inner surface 50 of the vessel wall 48.

In operation, a catheter as above described, of the appropriate size for the blood vessel or other cavity to be treated, is selected and inserted into a cavity or blood vessel and advanced to a selected area within the vessel to be treated. Once positioned at the selected spot in the vessel, a suitable source of inflating medium is connected to the inflation port and inflating medium, such as a gas or liquid is introduced into the interior of the inner balloon 28 to expand it until the outer surface of outer bladder 38 expands into surface contact with the walls of the vessel. This places the electrode formed by the coating 26 on the outer balloon 38 in direct surface contact with the interior surface of the blood vessel. An electrode 25 may be either placed in contact with the tissue surface or inserted into the tissue. The electrical conductors at the proximal end of the catheter are connected to a source of electrical power, such as a high voltage pulse generator.

A source of fluid containing drugs and/or genes are connected to the infusion inlet port 20 at the proximal end of the catheter and an appropriate amount of drugs or genes are infused through the tube 44 into the annular chamber 42 between the inner and outer bladders where it communicates through the ports 40 into surface contact with the vessel wall 50. Voltage pulses are then applied to the electrodes 24 and 26 to cause electroporation of the cells in the walls of the vessel and/or the tissue forming the walls of the vessel to enable the solution containing the genes or drugs to pass into the cells or tissue. Voltage may also be applied to electrode 25 and one of the other of electrode 24 and 26 to move the molecules further into the tissue and to electroporate cells in the tissue 48 away from the vessel walls 50. A suitable power source and a suitable source of fluid for infusion may be provided as disclosed in U.S. Pat. No. 5,507,724, which is incorporated herein by reference as though fully set forth. This balloon catheter construction provides an efficient and effective apparatus for introducing the drugs or genes into the tissue and cells of vessel wall and adjacent tissue and walls, and at the same time apply an appropriate electrical pulse to the tissue or cells for enabling the uptake of the drugs or genes by the cells, and/or tissue.

The electrode arrangement for the distal end of the catheter may take any suitable form, such as that illustrated in FIGS. 1–4, wherein the outer end 24 of the guide wire serves as one electrode of the system. Alternative arrangements may be made, such as illustrated, for example, in FIG.

5 wherein the inflatable cushion of the catheter is the same as that as in FIG. 2–4. However, the guide wire is exposed at a position on the interior of the inflatable balloon with the electrode defined by an exposed portion 52 of the guide wire on the interior of the balloon. The remainder of the guide wire is insulated as in the prior embodiment. In this configuration the inflating medium consists of a conductive liquid such as saline solution and the inner balloon or bladder 28 is made from a conductive elastic material.

Figure 6:
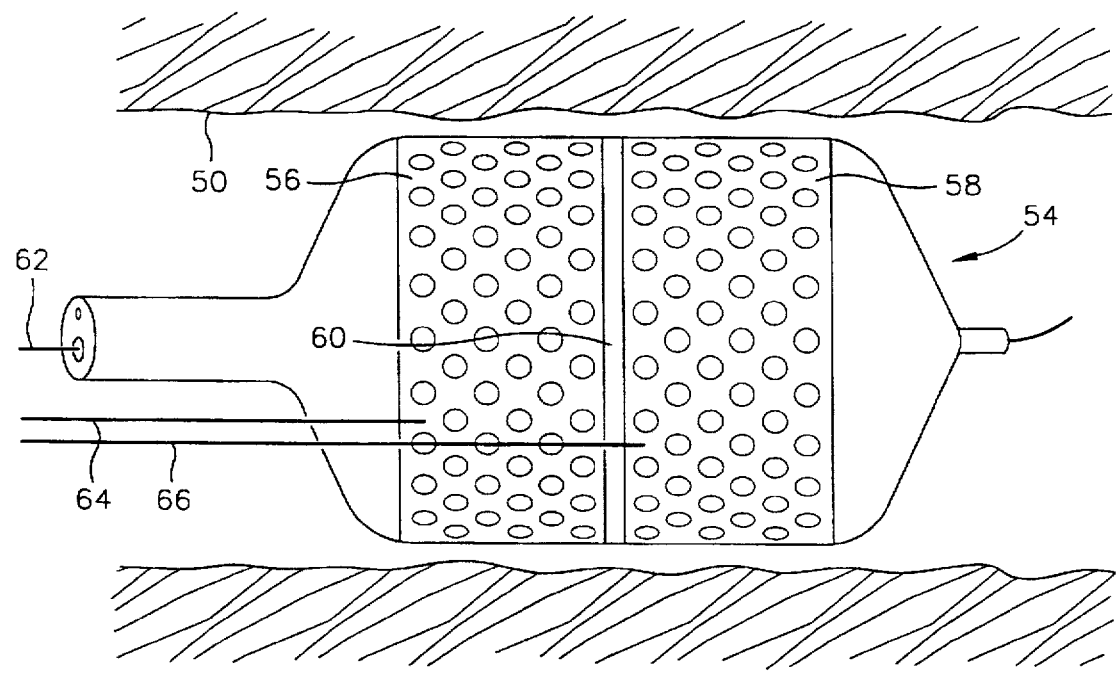
FIG. 6 is a view like FIG. 5 of another embodiment of the invention.

Referring now to FIG. 6, an alternate arrangement is illustrated wherein a distal end balloon assembly designated generally by the numeral 54, has a balloon construction substantially identical to that of FIG. 2, but with electrodes 56 and 58 formed as separated coatings on the outer surface of the balloon assembly with a spacing 60 therebetween serving as an insulator. In this construction the guide wire is fully insulated and does not serve as a conductor. Separate conductors 64 and 66 are provided for the separate electrodes 56 and 58. One advantage to this arrangement is that a known distance exists between the two electrodes.

Figure 7:
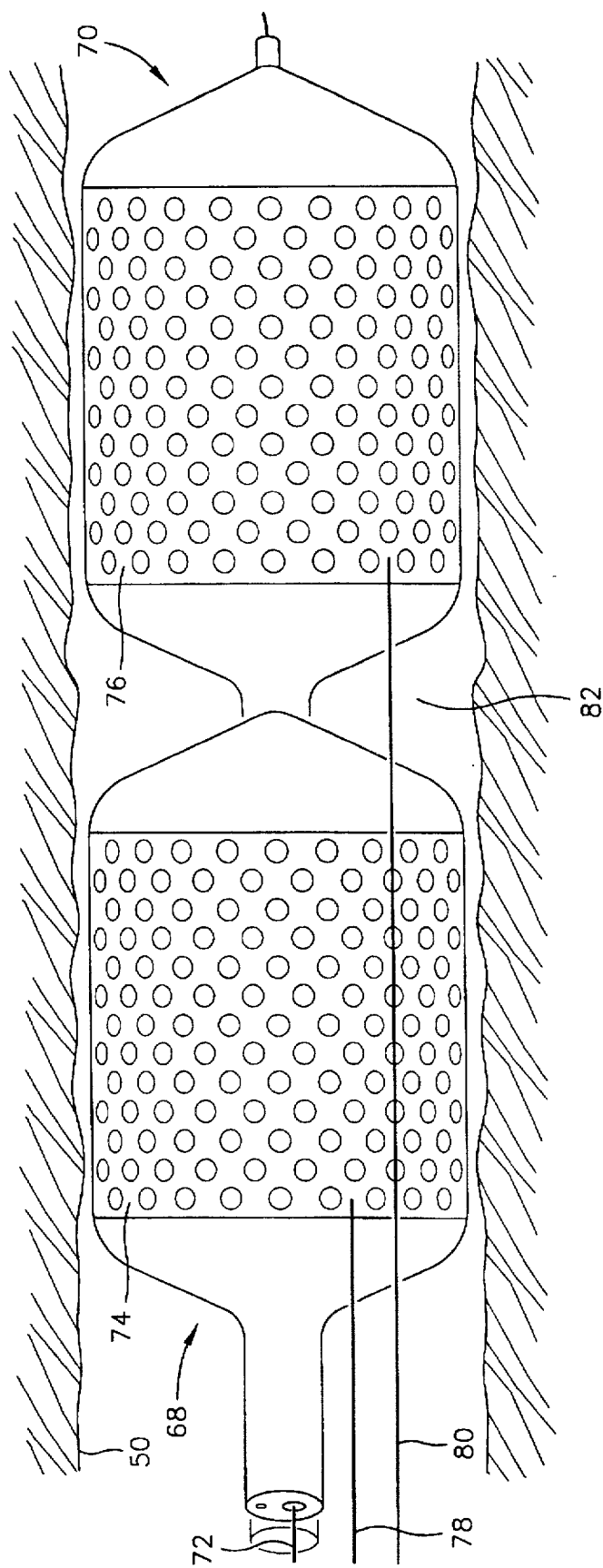
FIG. 7 is a view like FIG. 5 of a further embodiment of the invention.

Referring now to FIG. 7, there is illustrated an arrangement wherein the balloon assembly comprises a pair of spaced apart balloons 68 and 70 on an insulated guide wire 72. The electrodes comprise separate coatings 74 and 76 on the outer surface of each of the separate balloons 68 and 70. Each electrode is connected by a separate conductor 78 and 80 to the source of power. This arrangement can provide for covering a larger linear surface area of tissue for an application. In addition, it provides a space or chamber 82 between the two separate balloons 68 and 70, such that drugs or genes in suspension may be trapped or confined to that space and be introduced into the electroporation process. In addition, a specified distance is provided between the two electrodes, thereby providing a predetermined parameter for the process.

Figure 8:
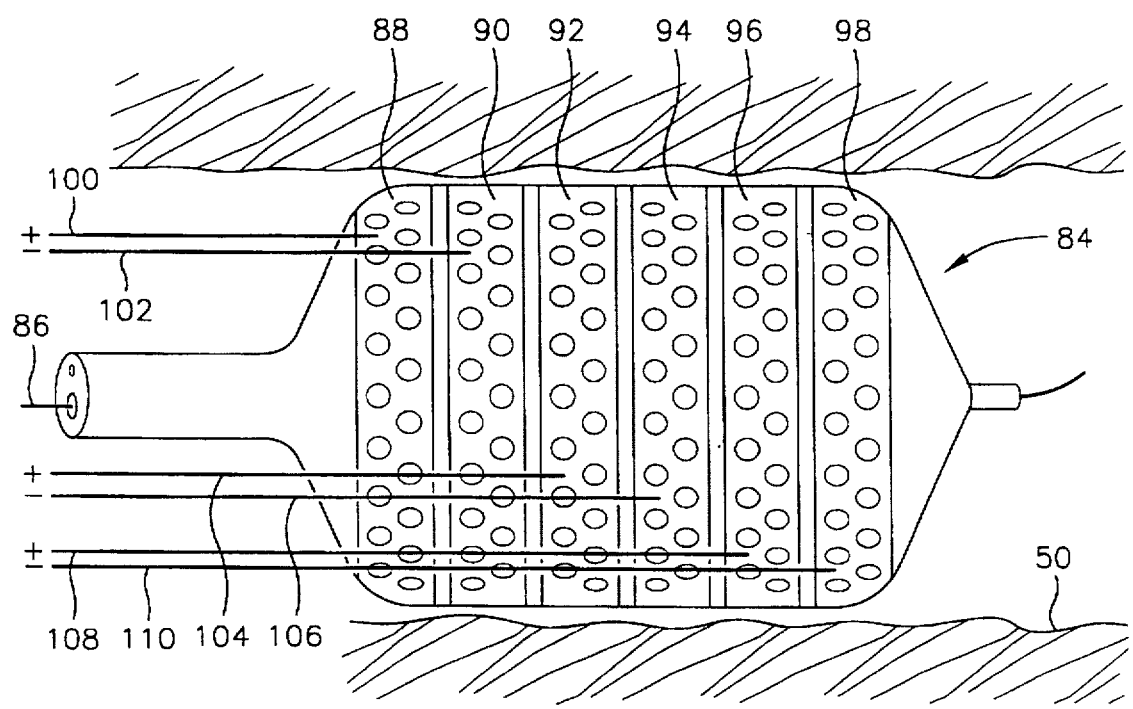
FIG. 8 is a view like FIG. 5 of a still another embodiment of the invention.

Referring to FIG. 8, a still further embodiment is illustrated wherein a balloon assembly, designated generally at 84, is mounted on a distal end of a guide wire 86 as in the prior embodiments. The balloon assembly is constructed in substantially the same manner as in the previous embodiments. The arrangement, however, is provided with multiple pairs of annular electrodes positioned along the length of the balloon assembly 84. In this arrangement, a pair of opposed electrodes 88 and 90 are disposed adjacent one another at one end of the balloon with an intermediate pair of electrodes 92 and 94 positioned approximate to the center of the balloon assembly. A final pair of electrodes, 96 and 98, are shown at the outermost end of the balloon. At least a pair of conductors 100 and 102 connect the respective pairs of conductors to a power source. The pairs of electrodes may be connected with the positive electrodes to a common conductor with the negative electrodes to another common conductor. In the alternative, they may be separately connected in pairs and may be sequentially or alternatively activated. We have found in certain applications that multiple pairs of electrodes alternatively and/or sequentially powered provide improved results.

Where genes are to be infused into the patient, the fluid medium is selected so that it will support the viability of the genes until they are inserted into the blood cells of the patient. Such fluid mediums are well known to those skilled in the art. The pump supplying the fluid may be the plunger of a syringe which may be pushed inwardly by a motor driven piston assembly. The rate of delivery of the fluid medium from the syringe through the injection tubes may be manually adjusted via controls with the delivery parameters being indicated on a display.

The function of the power source 50 is to generate predetermined voltage pulses which, when applied to the electrodes, result in applying electric fields of a predetermined amplitude and duration so that the drugs or genes can enter the tissue, endothelial or other cells via electroporation. Preferably, for electroporation, these fields are applied repeatedly and their amplitude and duration make the walls of the endothelial or other cells sufficiently permeable to permit the drugs or genes to enter the cells without killing them.

One suitable power pack for the system is the ELECTRO CELL MANIPULATOR Model ECM 600 voltage generator commercially available from the BTX Instruments Division of Genetronics, Inc. of San Diego, Calif., U.S.A. The ECM 600 voltage generator generates a pulse from the complete discharge of a capacitor which results in an exponentially decaying waveform. The voltage pulse generated by the ECM 600 voltage generator is characterized by a fast rise time and an exponential tail. In the ECM 600 voltage generator, the electroporation pulse length is set by selecting one of ten timing resistors marked R1 through R10. They are active in both High Voltage Mode (HVM) (capacitance fixed at fifty microfarad) and Low Voltage Mode (LVM) (with a capacitance range from 25 to 3,175 microfarad).

The application of an electrical field across the cell membrane results in the creation of transient pores which are critical to the electroporation process. The ECM 600 signal generator provides the voltage (in kV) that travels across the gap (in cm) between adjacent pairs of electrodes. This potential difference defines what is called the electric field strength where E equals kV/cm. Each cell species has its own critical field strength for optimum electroporation. This is due to cell size, membrane make-up and individual characteristics of the cell wall itself. For example, mammalian cells require typically between 0.5 and 5 kV/cm before cell death and/or electroporation occurs. Generally, the required field strength varies inversely to the size of the cell.

The ECM 600 signal generator has a knob that permits the adjustment of the amplitude of the set charging voltage applied to the internal capacitors from 50 to 500 volts in LVM and from 0.05 to 2.5 kV in the HVM. The maximum amplitude of the voltage pulses is shown on a display incorporated into the ECM 600 signal generator. This device further includes a plurality of push button switches for controlling pulse length, in the LVM, by a simultaneous combination of resistors parallel to the output and a bank of seven selectable additive capacitors.

The ECM 600 signal generator also includes a single automatic charge and pulse push button. This button may be depressed to initiate both charging of the internal capacitors to the set voltage and to deliver a pulse to the catheter device in an automatic cycle that takes less than five seconds. The manual button may be sequentially pressed to repeatedly apply the predetermined voltage pulse to the medium or a repetitive charge/pulse mode may be selected with an adjustable repetition rate. By selecting the electrical parameters of the pulses, the preferred insertion into endothelial cells is possible.

The waveforms of the voltage pulse provided by the generator in the power pack can be an exponentially decaying pulse, a square pulse, a unipolar oscillating pulse train or a bipolar oscillating pulse train. The electric field strength can be 0.2 kV cm to 20 k V/cm. The pulse length can be ten microseconds to one hundred milliseconds. There can be from one up to one hundred pulses applied to an area or a group of cells. Of course, the waveform, electric field strength and pulse duration are dependent upon the exact construction of the catheter device 10 and the type of molecules that are to enter the endothelial cells via electroporation.

After infusing the molecules into or through the bladder walls into contact with the vessel wall, electroporation can be performed generating locally high-intensity pulses of electric fields, for example between one electrode in the balloon and an electrode structure on the outside of the balloon, or electrode structures on the outside of the vessel. Thus, the method and apparatus of the present invention provides a highly flexible apparatus and technique for gene and drug therapy and treatment.

EXAMPLE

Experiments were conducted with a balloon catheter which had the balloon surface coated with Ag/AgCl conductive paste as one electrode and a distal wire loop as the second electrode, substantially as illustrated in FIG. 1. The balloon was made porous by piercing the balloon (including the metal coating) 20–25 times in 4 equally-spaced rows of 5–7 holes around the balloon circumference, using a #21 gauge needle.

Pigs (Sus scrofa) were sedated, then intubated and maintained under general anesthesia. A surgical cutdown was performed on the right or left femoral artery and a vascular introducer was placed. The animals were given heparin 200 units/kg to prevent blood coagulation on the catheters and ballooned arteries. Using fluoroscopic visualization, a guiding catheter was used to place an exchange guidewire into the right or left common carotid artery. The guide catheter was then removed leaving the guidewire in place, and the prototype electroporation catheter was introduced and advanced into the site selected for treatment, which was marked for subsequent tissue harvest by placement of a radiopaque clamp on the skin surface adjacent to the site. Assignment to control or treatment group was made by constrained randomization.

A generator ECM 600, manufactured by BTX, a division of Genetronics, Inc., San Diego, Calif., was used to generate the pulsed electric fields. The voltage setting was kept constant at 100 V, with a pulse length setting of 1.5 msec. Five pulses were typically given a few seconds after balloon inflation with propidium iodide solution (20 µg/ml). Control arteries were treated in an identical fashion except that no current was applied.

After balloonings were completed, the catheter was removed and the segments of carotid artery were excised as specimens. The specimens were rinsed with heparinized 0.9% NaCl solution and cut into 6–8 arterial ring segments approximately 2–3 mm in length. These were embedded in O.C.T. and snap-frozen in 2-methyl butane cooled to liquid $N_2$ temperature. Cross-sections (6 µm) were cut on a cryotome and collected on glass slides. They were imaged without further staining on a Nikon microscope equipped with a 100 W mercury lamp and 35 mm camera back. The specimens were viewed and photographed at two fluorescent wave lengths: 1) excitation filter with 470–490 nm wave length, maximum specimen emission at 525 nm without a barrier filter; 2) excitation at 510–560 nm, maximum emission at 615 nm. This imaging strategy allowed: 1) discrimination of the zones of most intense propidium iodide fluorescence at the 525 nm emission by 'spillover', whereby the yellow-green autofluorescence of the arterial wall contrasted with the orange propidium iodide fluorescent signal; and 2) comparison of the relative intensity of the signal from regions of interest at the red, 615 nm wave length. Qualitative analysis was made and representative documentation recorded.

RESULTS

Fluorescence microscopy demonstrated markedly and consistently higher propodium iodide fluorescence in the pulse treated artery compared to the control. Most of the DNA-binding marker was concentrated in smooth muscle cells throughout the tunica media in the treated artery, but most of the marker which was detected in the control artery was present in remnant endothelium or the most luminal 1–2 smooth muscle cell layers of the media.

These experiments demonstrated proof of principle that concomitant application of high field strength, brief duration electrical pulses during saturation of the arterial wall with DNA-binding, low-molecular weight fluorescent marker compound in solution via a catheter device, enhances the tissue and cellular uptake of that compound compared to saturation alone.

While we have described preferred embodiments of our catheter device and our method for drug and gene delivery to endothelial cells, it should be understood that modifications and adaptations thereof will occur to persons skilled in the art. Therefore, the protection afforded our invention should only be limited in accordance with the scope of the following claims.

We claim:

1. An electroporation apparatus for introducing molecules into cells at a selected location within a cavity in the body of a patient, comprising:
    an elongated catheter having a proximal end and a distal end and a guide wire extending from said proximal end to said distal end;
    an inflatable balloon carried by said distal end, said balloon having an inner inflatable bladder and an outer perforated bladder defining a chamber therebetween;
    means defining a first electrode on an outer surface of the inflatable portion of said outer perforated bladder;
    means associated with said distal end defining a second electrode spaced from said first electrode;
    means for delivering a predetermined quantity of a fluid medium carrying preselected molecules into said chamber to be infused into said body cavity at the predetermined location; and
    means for applying a voltage pulse between said first electrode and said second electrode for repeatedly generating electric fields of a predetermined amplitude and duration inducing the walls of a plurality of cells at the predetermined location to be transiently permeable to enable the molecules to enter said cells.

2. An apparatus according to claim 1 wherein said means defining a first electrode on an outer surface of said outer perforated bladder is a conductive coating on said outer surface.

3. An apparatus according to claim 1 wherein said means defining a first electrode on an outer surface of said outer perforated bladder comprises a conductive elastomeric material defining said outer bladder.

4. An apparatus according to claim 3 wherein said means defining a second electrode comprises an exposed portion of said guide wire.

5. An apparatus according to claim 1 wherein said means defining a second electrode comprises an exposed portion of said guide wire.

6. An apparatus according to claim 5 wherein said exposed portion of said guide wire is exterior of said inflatable balloon.

7. An apparatus according to claim 5 wherein said exposed portion of said guide wire is interior of said inflatable balloon.

8. An apparatus according to claim 1 wherein said means defining a second electrode comprises a conductive coating on said outer surface.

9. An apparatus according to claim 8 wherein said means defining a first electrode comprises a conductive coating on said outer surface.

10. An apparatus according to claim 9 wherein said conductive coating defining said first electrode and said conductive coating defining said second electrode each comprises a band around said outer surface.

11. An apparatus according to claim 1 further comprising at least a third and a fourth electrodes.

12. An apparatus according to claim 1 further comprising another inflatable balloon carried by said distal end, said another balloon having an inner inflatable bladder and an outer perforated bladder defining a chamber therebetween, and wherein said second electrode is defined by an outer surface of said outer bladder of said another balloon.

13. An apparatus according to claim 1 wherein the means for applying a voltage pulse between said first electrode and said second electrode for repeatedly generating electric fields of the voltage pulse having a wave form selected from the group consisting of an exponentially decaying pulse, a square pulse, a unipolar oscillating pulse train and a bipolar oscillating pulse train, the electric field having a strength of between approximately 0.2 kV/cm and 20.0 kV/cm, and each pulse having a duration of between approximately ten microseconds and one hundred milliseconds.

14. A catheter according to claim 1 further comprising another inflatable balloon carried by said distal end, said another balloon having an inner inflatable bladder and an outer perforated bladder defining a chamber therebetween, and said outer bladder having a conductive outer surface defining said second electrode.

15. A catheter according to claim 1 further comprising a remote electrode external to said catheter.

16. A catheter according to claim 15 wherein said remote electrode is a penetrating electrode.

17. An electroporation catheter for introducing molecules into cells at a selected location within a cavity in the body of a patient, comprising:

an elongated catheter having a proximal end and a distal end and a guide wire extending from said proximal end to said distal end;

an inflatable balloon carried by said distal end, said balloon having an inner inflatable bladder and an outer perforated bladder having perforations defining a chamber therebetween;

said outer perforated bladder having a conductive outer surface defining a first electrode on the inflatable portion of said perforated bladder for engagement with walls of said cavity;

a second electrode spaced from said first electrode carried by Said distal end of said catheter;

means for delivering a predetermined quantity of a fluid medium carrying preselected molecules into said chamber for infusing via said perforations into said cavity at the predetermined location; and conductor means at said proximal end of said catheter for connecting to a power source for applying a voltage pulse between said first electrode and said second electrode for repeatedly generating electric fields of a predetermined amplitude and duration inducing the walls of a plurality of cells at the predetermined location to be transiently permeable to enable the molecules to enter said cells.

18. A catheter according to claim 17 wherein said conductive outer surface comprises a coating on said outer surface.

19. A catheter according to claim 18 wherein said conductive outer surface comprises a conductive elastomeric material defining said outer bladder.

20. A catheter according to claim 18 wherein said means defining a second electrode comprises a conductive coating on said outer surface spaced from said first conductive surface.

21. A catheter according to claim 20 wherein said conductive coating defining said first electrode and said conductive coating defining said second electrode each comprises a band around said outer surface.

22. A catheter according to claim 17 wherein said means defining a second electrode comprises a second conductive outer surface spaced from said first surface.

23. A catheter according to claim 17 further comprising means for applying a voltage pulse between said first electrode and said second electrode for repeatedly generating electric fields, the voltage pulse having a wave form selected from the group consisting of an exponentially decaying pulse, a square pulse, a unipolar oscillating pulse train and a bipolar oscillating pulse train, the electric field having a strength of between approximately 0.2 kV/cm and 20.0 kV/cm, and each pulse having a duration of between approximately ten microseconds and one hundred milliseconds.

24. A catheter according to claim 17 further comprising a remote electrode external to said catheter.

25. A catheter according to claim 24 wherein said remote electrode is a penetrating electrode.

* * * * *